(12) United States Patent
Bertrand-Drira et al.

(10) Patent No.: US 12,350,649 B2
(45) Date of Patent: Jul. 8, 2025

(54) METHOD FOR PREPARING A CATALYST SUPPORT

(71) Applicant: IFP Energies Nouvelles, Rueil-Malmaison (FR)

(72) Inventors: Chloe Bertrand-Drira, Rueil-Malmaison (FR); Aurelie Dandeu, Rueil-Malmaison (FR); Severine Humbert, Rueil-Malmaison (FR); Mehdi Le Moel, Rueil-Malmaison (FR); Thomas Regal, Rueil-Malmaison (FR); Fabien Salvatori, Rueil-Malmaison (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 694 days.

(21) Appl. No.: 17/770,702

(22) PCT Filed: Oct. 7, 2020

(86) PCT No.: PCT/EP2020/078171
§ 371 (c)(1),
(2) Date: Apr. 21, 2022

(87) PCT Pub. No.: WO2021/078522
PCT Pub. Date: Apr. 29, 2021

(65) Prior Publication Data
US 2022/0410127 A1    Dec. 29, 2022

(30) Foreign Application Priority Data

Oct. 22, 2019  (FR) ...................................... 1911785

(51) Int. Cl.
*B01J 21/12*    (2006.01)
*B01J 35/50*    (2024.01)
(Continued)

(52) U.S. Cl.
CPC ............... *B01J 21/12* (2013.01); *B01J 35/50* (2024.01); *B01J 37/0045* (2013.01);
(Continued)

(58) Field of Classification Search
CPC ........ B01J 21/12; B01J 35/50; B01J 37/0045; B01J 37/0236; B01J 37/038; B01J 37/04; B01J 37/50
(Continued)

(56) References Cited

U.S. PATENT DOCUMENTS 2,045,519 A * 6/1936 Gould ...................... F01N 3/04
95/227
3,034,995 A * 5/1962 Braithwaite ............. B01J 21/16
502/238

(Continued)

FOREIGN PATENT DOCUMENTS

EP    1126008 A1    8/2001
EP    1485069 B1    12/2014
(Continued)

OTHER PUBLICATIONS

International Search Report PCT/EP2020/078171 dated Dec. 8, 2020 (pp. 1-3).

*Primary Examiner* — Cam N. Nguyen
(74) *Attorney, Agent, or Firm* — Csaba Henter; MILLEN, WHITE, ZELANO & BRANIGAN

(57) ABSTRACT

A process for preparing a powder support containing alumina and silica or their derivatives for a catalyst of a Fischer-Tropsch type reaction, including stage (a) of preparing a first reactant containing an alumina compound or precursor including a reaction for peptization of an alumina compound or precursor in the presence of an acid, to form solid particles in suspension, stage (b) of preparing a second reactant based on silicic acid and/or on a compound or
(Continued)

precursor of silicic acid, including a controlled aging treatment of the silicic acid targeted at its polymerization up to a degree of conversion of the silicic acid of at most 70%, stage (c) of mixing the two reactants in a mixer, and the pH of the first reactant is adjusted to a value not exceeding a given maximum pH threshold.

20 Claims, 2 Drawing Sheets

(51) Int. Cl.
| | |
|---|---|
| *B01J 37/00* | (2006.01) |
| *B01J 37/02* | (2006.01) |
| *B01J 37/03* | (2006.01) |
| *B01J 37/04* | (2006.01) |
| *C07C 1/04* | (2006.01) |

(52) U.S. Cl.
CPC ......... *B01J 37/0236* (2013.01); *B01J 37/038* (2013.01); *B01J 37/04* (2013.01); *C07C 1/043* (2013.01); *C07C 1/0445* (2013.01); *C07C 2521/04* (2013.01)

(58) Field of Classification Search
USPC .......................... 502/240, 355, 415
See application file for complete search history.

(56) References Cited

U.S. PATENT DOCUMENTS

| | | | | |
|---|---|---|---|---|
| 4,242,236 A | * | 12/1980 | Blakely | B01J 21/12 |
| | | | | 502/439 |
| 4,289,653 A | * | 9/1981 | Jaffe | C10G 45/08 |
| | | | | 502/255 |
| 4,705,767 A | * | 11/1987 | Cheng | B01J 21/04 |
| | | | | 502/355 |
| 4,988,659 A | * | 1/1991 | Pecoraro | B01J 21/12 |
| | | | | 502/235 |
| 5,001,097 A | | 3/1991 | Pecoraro | |
| 5,135,641 A | * | 8/1992 | Pecoraro | B01J 21/12 |
| | | | | 208/46 |
| 6,465,530 B2 | | 10/2002 | Roy-Auberger et al. | |
| 6,787,501 B2 | * | 9/2004 | Vaughn | C07C 7/08 |
| | | | | 502/64 |
| 6,872,685 B2 | * | 3/2005 | Timken | B01J 21/12 |
| | | | | 502/263 |
| 6,995,112 B2 | * | 2/2006 | Timken | C10G 45/60 |
| | | | | 502/355 |
| 7,008,644 B2 | | 3/2006 | Batycky et al. | |
| 7,238,331 B2 | | 7/2007 | Zhou et al. | |
| 7,517,827 B2 | * | 4/2009 | Ravichandran | B01J 29/70 |
| | | | | 502/68 |
| 8,084,387 B2 | | 12/2011 | Jun et al. | |
| 9,617,480 B2 | * | 4/2017 | Shu | B01J 35/38 |
| 10,196,326 B2 | * | 2/2019 | Ramello | C07C 1/24 |
| 11,118,159 B2 | * | 9/2021 | Hirt | C12N 1/205 |
| 11,642,664 B2 | * | 5/2023 | Yu | B01J 35/647 |
| | | | | 208/213 |
| 2003/0136707 A1 | | 7/2003 | Harris et al. | |
| 2004/0014917 A1 | | 1/2004 | Eberle et al. | |
| 2014/0007493 A1 | * | 1/2014 | Henry | B01J 37/0045 |
| | | | | 502/64 |

FOREIGN PATENT DOCUMENTS

| | | |
|---|---|---|
| WO | 2005058493 A1 | 6/2005 |
| WO | 2020187545 A1 | 9/2020 |

* cited by examiner

METHOD FOR PREPARING A CATALYST SUPPORT

TECHNICAL FIELD

The present invention relates to the field of catalysts used for reactions for the synthesis of hydrocarbons starting from a gas mixture comprising carbon monoxide and hydrogen, generally known as the Fischer-Tropsch synthesis.

PRIOR ART

Fischer-Tropsch synthesis processes make it possible to obtain a wide range of hydrocarbon cuts starting from the $CO+H_2$ mixture, commonly known as synthesis gas. The overall equation of the Fischer-Tropsch synthesis can be written in the following way:

$$nCO+(2n+1)H_2 \rightarrow C_nH_{2n+2}+nH_2O$$

The Fischer-Tropsch synthesis is at the heart of processes for the conversion of natural gas, coal or biomass into fuels or into intermediates for the chemical industry. These processes are known as GTL (Gas to Liquids) in the case of the use of natural gas as starting feedstock, CTL (Coal to Liquids) for coal, and BTL (Biomass to Liquids) for biomass.

In each of these cases, the starting feedstock is first of all gasified to give a synthesis gas which comprises a mixture of carbon monoxide and molecular hydrogen. The synthesis gas is subsequently converted mainly into paraffins by virtue of the Fischer-Tropsch synthesis, and these paraffins can subsequently be converted into fuels by a hydroisomerization-hydrocracking process. For example, processes for the conversion, such as hydrocracking, dewaxing and hydroisomerization, of heavy (C16+) cuts make it possible to produce various types of fuels in the middle-distillate range: gas oil (180-370° C. cut) and kerosene (140-300° C. cut). The lighter C5-C15 fractions can be distilled and used as solvents.

The Fischer-Tropsch synthesis reaction can be carried out in various types of reactors (fixed, moving or three-phase (gas, liquid, solid) bed, for example of perfectly stirred autoclave or slurry bubble column type), and the reaction products exhibit in particular the characteristic of being devoid of sulfur compounds, nitrogen compounds or compounds of aromatic type.

In one embodiment in a reactor of slurry bubble column type (or else "slurry" type in a simplified expression), which employs a divided catalyst in the form of a very fine power, typically of the order of a few tens of micrometers, this powder forms a suspension with the reaction medium.

The Fischer-Tropsch reaction takes place in a conventional way between 1 and 4 MPa (10 and 40 bar), at temperatures conventionally of between 200° C. and 350° C. The reaction is exothermic overall, which requires particular attention to the employment of the catalyst, which is furthermore also subject to particularly severe conditions in terms of mechanical and chemical stress.

The catalysts employed for the Fischer-Tropsch synthesis generally consist of supports, for example made of silica or alumina, which are combined with one or more active agents, which are deposited at the surface of the supports (and/or which can impregnate these supports over a certain thickness). These are then referred to as supported metal catalysts. These active agents are generally metallic, in particular based on cobalt or iron. The conventional methods for the preparation of these supported metal catalysts used for the Fischer-Tropsch synthesis consist in depositing a metal salt or a metal-ligand coordination complex on the support and in then carrying out one or more heat treatment(s) carried out under air, followed by a reducing treatment carried out ex situ or in situ.

The invention will be concerned more particularly with the preparation of supports for these catalysts, in particular supports comprising a mixture of alumina and silica (hydrated or not).

The document EP 2 173 481 describes, for example, the preparation of a support based on alumina alone, which also includes a phosphorus promoter, presented as making it possible to improve the hydrothermal resistance of a catalyst in a Fischer-Tropsch reaction. The preparation comprises the mixing of a solution of aluminum alkoxide dissolved in an alcohol-based organic solvent, of an organic carboxylic acid having a pKa of 3.5 to 5 and of water, and then the heating of the whole at a temperature of 80 to 130° C. in order to prepare a boehmite sol. This sol is subsequently dried and then baked at a temperature of 400 to 700° C. in order to prepare alumina having a specific surface in the range from 300 to 800 m²/g, which will subsequently be treated in order to incorporate the phosphorus promoter therein.

Silica-alumina mixture supports are furthermore sold by Sasol under the name Siral for silica-alumina hydrates, and under the name Siralox for their corresponding oxides.

It has hitherto been known to prepare alumina-silica mixture supports by batch processes, with the preparation of a stirred vessel suspension starting from the alumina-based reactant or from its precursor, and from the silica precursor in the silicic acid form. It turns out that the control of the reaction in the vessel is problematic because the suspension exhibits a complex rheology, in particular during the introduction of the silicic acid into the vessel, there being a risk of the acid crosslinking to form an irreversible gel. There is thus a real difficulty in controlling the change in viscosity in the vessel, all the more so as the following stage consists in recovering the suspension in order to dry it by atomization, an operation which requires having, at the outlet of the vessel, a suspension with a viscosity which is well controlled and which does not exceed a critical threshold beyond which the suspension can no longer be atomized.

The patent application WO 2005/058493 recommends producing particles using silicic acid prepared from a precursor, and which is added to the alumina or its precursor as soon as it is ready to be used, eliminating or limiting as much as possible its storage time before use. The aim is to avoid or minimize its polymerization, which, according to this document, makes it less reactive with respect to the alumina or its precursor. It is thus necessary to use silicic acid which is as "fresh" as possible. This recommendation is restrictive industrially.

An aim of the invention is therefore to develop an improved process for the preparation of a Fischer-Tropsch catalyst support based on silica-alumina, which process overcomes the abovementioned disadvantages. It is thus a matter of providing a new process which is, in particular, more robust and more reproducible, which makes possible production on the industrial scale in a shorter time with the same quality of final product, indeed even a higher quality, or also which makes possible greater flexibility in its implementation. Subsidiarily, another aim of the invention is to obtain such a support which can exhibit a maintained or improved hydrothermal resistance, and/or to obtain such a support in the form of a powder with a precise and reproducible dimensional grading.

SUMMARY OF THE INVENTION

A subject matter of the invention is first of all a process for the preparation of a support for a catalyst of a reaction of Fischer-Tropsch type in the form of a powder, said support comprising alumina and silica or their derivatives, starting from:
- a first reactant comprising an alumina compound or precursor, and optionally alumina, in suspension in a solvent, in particular an aluminum oxyhydroxide,
- and a second reactant based on silicic acid and/or on a compound or precursor of silicic acid, and optionally silica, in suspension or dissolved in a solvent.

According to the invention, the process comprises:
- a stage (a) of preparation of the first reactant in a first reactor (10), including a reaction for peptization of an alumina compound or precursor, in particular of an aluminum oxyhydroxide, in the presence of an acid, so as to form solid particles in at least partially colloidal suspension,
- a stage (b) of preparation of the second reactant in a second reactor (20), including a controlled aging treatment of the silicic acid targeted at its polymerization up to a degree of conversion of the silicic acid of at most 70%,
- a stage (c) of mixing the two reactants resulting from the two reactors in a mixer or group of mixers, in which the reaction between the two reactants takes place, in order to obtain a mixture in the form of particles in suspension in a liquid phase.

The method also provides for adjusting the pH of the first reactant to a value not exceeding a given maximum pH threshold ($pH_{max}$) before its introduction into the mixer in the mixing stage (c).

Advantageously, the process comprises/consists of stages (a), (b) and (c), with the adjustment of the pH of the first reactant.

Preferably, the solvents used are aqueous or essentially aqueous. They are in any case miscible/compatible with one another.

This mode of synthesis has proven to be highly advantageous, combining two process characteristics in order for the mixture of the two reactants to exhibit a sufficiently controlled and sufficiently reproducible viscosity to guarantee the operability of the production of this catalyst support. This control of the viscosity during the mixing stage allows the mixture to be shaped in order to obtain the support particles expected by the "atomization" technology, which does not tolerate excessively variable/excessively high viscosities.

With the invention, a better stability of the mixture of the two reactants is obtained: the viscosity of the mixture is lower, and it rises later, compared to the mixture of the reactants encountered in the prior art.

The first characteristic of the invention is the control of the pH of the first reactant, comprising the alumina compound or precursor, which makes it possible to control/stabilize the viscosity thereof and consequently to influence that of the mixture with the second reactant up to the end of the mixing stage: to thus impose a maximum (acid) pH threshold makes it possible for the pH of the first reactant not to exceed the isoelectric point of the second, in particular silicic acid, which would have the beneficial and unexpected effect of combating the increase in viscosity of the first reactant and then of the mixture as observed in the prior art.

The second characteristic of the invention is the controlled aging of the second reactant, based on silicic acid, in order to succeed in stabilizing its viscosity before mixing with the first reactant. Instead of imposing the constraint of using a "fresh" silicic acid for the mixing, which would thus have to be produced on request without intermediate storage, the invention deliberately ages the silicic acid, by appropriate operating conditions, in terms of temperature and of duration of treatment in particular, in order for it to be partially converted into condensed/polymerized silicic acid and be stabilized. It is thus possible to store this stabilized product, or to use it directly after its aging, keeping constant or virtually constant the operating conditions for the mixture and the continuation of its treatment, with a reactivity of the silicic acid, even partially condensed, which remains excellent, which is surprising because it might have been thought that this condensed silicic acid would be (significantly) less reactive.

With the invention, there is thus finally easy access to this atomization technology, which is the only one which, industrially, makes it possible to obtain particles having the desired particle size distribution, geometry and reproducibility. It is then possible to obtain particles which behave better hydrodynamically and it is easier to measure the dimensions of their grains (easier measurement of a diameter or a pseudodiameter than taking the dimensions of an irregular grain). The powder obtained in the end has also proved to show a very satisfactory hydrothermal resistance, a very important point in view of its final use in the Fischer-Tropsch process.

Preferably, the controlled aging treatment is carried out at a temperature of between 5° C. and 90° C., in particular 5° C. and 20° C. or greater than 20° C. and at most 85° C., in particular between 35° C. and 75° C., preferably between 45° C. and 65° C. This is because the aging according to the invention can be done either under cold conditions or at ambient temperature (5-20° C., for example), optionally while providing appropriate cooling means, or under "hot" conditions, that is to say at more than 20° C. and in particular at more than 30° C., optionally with appropriate heating means.

Advantageously, the appropriate heating (and/or cooling) means are thus provided as a function of the initial temperature of the silicic acid solution before treatment.

The duration of the aging can also be adjusted between 1 minute and 72 hours. A person skilled in the art adjusts the duration of the treatment as a function of the temperature, it being known that the chosen duration can be shorter the higher the chosen temperature. Thus, an aging at at least 45° C. may last for only one to a few hours, less than 24 hours in any case, while an aging at less than 45° C. will preferably last longer, although preferably remaining at most 48 or at most 72 hours.

It should be noted that the temperature at which the aging takes place can be done in stationary phases, with a gradual rise in temperature, a stationary phase then a drop in temperature in order for the second reactant to be at the appropriate temperature for the mixing stage c).

Preferably, the controlled aging treatment is carried out up to a degree of conversion of the silicic acid of at least 10%, in particular of between 10% and 40%. It is thus seen that, even with a significant degree of condensation/polymerization, silicic acid, contrary to what was expected, remains an effective reactant.

Preferably, the controlled aging treatment is carried out at a concentration of silicic acid in the liquid phase of the second reactant of between 30 g/l and 200 g/l, in particular between 40 g/l and 60 g/l, for example approximately 50 g/l.

This controlled aging treatment is carried out batchwise, in a closed reactor, or continuously, in particular with a thermostatically controlled plug-flow reactor.

Preferably, the pH of the first reactant is adjusted to a value close to the isoelectric point of silicic acid, to at most 3.4, preferably to a pH of at most 3.2 or at most 3.1 and for example of between 2.8 and 3.2. The pH of the first reactant is thus adjusted, preferably to approximately +/−15%, in particular +/−10%, of the isoelectric point of silicic acid, which is 3.

Preferably, the pH of the first reactant can be adjusted during all or part of stage (a) of its preparation and/or at the end of stage (a) and/or after stage (a) and before stage (c). It is thus preferred, but not essential, to control the pH of the first reactant from its formation in stage (a) until its use in stage (c). What is recommended is in fact to control and, if appropriate, modify the pH of the first reactant when it is going to be mixed with the second reactant, and the time elapsing between the end of stage (a) and the start of stage (c) will guide the most appropriate choice, the viscosity of the first reactant tending to increase over time.

In a preferred embodiment of the invention, stage (a) is a reaction for peptization of an aluminum oxyhydroxide in the boehmite form, in the presence of an acid, in particular of nitric acid, so as to form solid particles in at least partially colloidal suspension.

Peptization is understood to mean a process responsible for the formation of a stable dispersion of colloidal particles in an aqueous-type solvent. (Peptization is also used during the synthesis of nanoparticles in order to make it possible for a large grouping of particles to split into several primary particles). This peptization is obtained by changing the surface state of the particles, by applying a charge or by adding a surfactant.

In the context of the invention, and in particular in the case of the boehmite gels with which the invention is more particularly concerned, an acid is used to carry out this peptization, the acid being adsorbed on the crystalline phases of the grains, and charging them.

In the case of the boehmite gels in particular, this dispersion in colloidal form can be total or partial.

In particular in this embodiment, the pH threshold ($pH_{max}$) of the first reactant, in particular an aluminum oxyhydroxide peptized in the form of solid particles in at least partially colloidal suspension, is set to at most 3.4 and is in particular of approximately 3. In fact, the peptization takes place in an acid medium but the invention has shown that it is by maintaining the pH at such low values during the manufacture of the first reactant, or at the very least by reducing it to such values when it is mixed with the second reactant, that the desired effect on the viscosity of the mixture is obtained.

Advantageously, the second reactant is maintained at a pH of at most 3.4, in particular of at most 3.2, for example between 2.9 and 3.1. In this case again, the second reactant is acidic, but the acid pH is preferably set at such low values in order to make its pH as close as possible to and as compatible as possible with the pH of the first reactant, so that their mixture, whatever the ratio between the two reactants, remains at low pH values (and in particular at a value of at most the $pH_{max}$ threshold value of the first reactant). The pH of the first reactant is thus close to, and preferably of at most, the value of the isoelectric point of silicic acid, which is in the vicinity of 3, which promotes good peptization and the maintenance of the viscosity of the mixture obtained at relatively low values.

Preferably, the mixing stage (c) takes place continuously in the mixer or the group of mixers in which the reaction between the two reactants takes place. This mode of synthesis of support continuously has proved to be very advantageous, insofar as it avoids any intermediate storage of the first reactant at the end of stage (a): when a stage of peptization of aluminum hydrate is concerned, it turns out that intermediate storage tends to raise the pH (and viscosity) of the reactant, significantly and not necessarily reproducibly. Mixing as a continuation of the stage of the preparation of the first reactant prevents/limits this change and thus prevents having to readjust the pH before mixing.

The invention has shown that regulation of the pH of the first reactant and a controlled aging of the second reactant, combined with a continuous mixing stage, gave the best results, both in terms of ease of production and, subsequently, in terms of shaping the mixture into grains.

Preferably, the mixing stage (c) takes place with regulation of the input flow rates of the first and second reactants at the inlet of said mixer/group of mixers, in particular carried out by subjecting one of the flow rates of reactants to the control of the other.

It is possible to regulate the input flow rates of the first and second reactants in stage (c) so as to maintain a ratio by volume of the flow rate of the first reactant to the flow rate of the second reactant of between 2 and 4, in particular between 2.8 and 3.6, preferably from 3.1 to 3.3. This ratio makes it possible to adjust as well as possible the final ratio of silica to aluminum derivatives in the catalyst support, in particular for a concentration by weight of 10% for each of the reactants in their respective liquid phases.

Advantageously, the viscosity of the mixture produced in stage (c) is kept less than or equal to 300 cP, in particular less than or equal to 250 cP, preferably at most 30 or 40 cP.

Preferably, the viscosity of the second reactant before aging is generally between 10 and 20 cP. After aging, the aim is a stable viscosity, higher than before aging but which remains at most 250 cP, in particular at most 100 cP.

The viscosity measurement is carried out at atmospheric pressure at ambient temperature, with shearing at 30 s$^{-1}$. The temperature can be regulated (in the examples, it is regulated at approximately 10° C.).

This viscosity range guarantees, in particular, that the subsequent atomization stage takes place under good conditions, with the possibility of forming a spray. As seen above, it is by adjusting the pH of the first reactant and by stabilizing the silicic acid, optionally combined with continuous mixing, that success is precisely achieved in maintaining the viscosity of the mixture within these ranges.

Advantageously, the process according to the invention also comprises: —a stage (d) which takes place continuously following the mixing stage (c), stage (d) being a stage of drying by atomization of the product resulting from the mixing stage (c) in order to obtain a powder.

As mentioned above, this stage generally requires having a suspension of particles/grains in a liquid phase with an imposed maximum viscosity, which could present a problem with the previous batch processes, whereas, with the process of bringing the two reactants into contact continuously according to the invention, success is achieved in controlling the viscosity of the suspension before introduction into the atomization device and in maintaining it below the required threshold much more easily.

Advantageously, the process according to the invention can also generally comprise a stage (e) of calcination of the powder obtained in stage (d), in particular at a temperature of between 900 and 1200° C., optionally followed by a sieving stage (f).

Advantageously, in stage (a), the initial concentration by weight of alumina compound or precursor (derivative) is chosen between 5% and 30%, in particular between 10% and 20%.

Preferably, stage (a) and/or stage (b) is carried out in a reactor equipped with an inlet, an outlet and a line for recycling from the outlet back into the reactor, in particular below the liquid level in said reactor. This recycling is optional and can serve as means for regulating the flow rate leaving the reactor under consideration (indeed even as stirring means for the reactor under consideration).

Also preferably, stage (a) is carried out in the first reactor equipped with stirring means, chosen in particular from stirring impellers and turbines with inclined blades. These stirring means make it possible to avoid sedimentation and can be active (mechanical stirrers with moving elements) or passive, with a carefully designed flow in the reactor in order to cause turbulence.

Advantageously, stage (b) of preparation of the second reactant uses a second reactor provided with stirring and thermal regulation (heating/cooling) means. The stirring means can be of the same type, active or passive, as those equipping the reactor used for stage (a). The thermal regulation means are useful for controlling the degree of aging of the silicic acid with which the invention is more particularly concerned. The stirring means ensure the thermal homogeneity of the liquid phase in the reactor.

The process according to the invention preferably also comprises:
  a stage (e) preliminary to stage (b), which is a stage of preparation of the silicic acid, when it is the latter which is chosen as second reactant, from silicate, in particular alkali metal silicate of sodium silicate type, which is passed through an ion exchange resin in order to remove the alkali metals.

Preferably, the residence time of the reactants in the mixer or group of mixers in stage (c) is at most 3 hours, in particular at most 3000 seconds or at most 2000 seconds. This will be a crossing time when mixing is carried out continuously.

Preferably again, stage (c) of mixing, in particular continuously, is carried out with several, in particular two, mixers in series, preferably static mixers, or with a disperser in series with at least one, preferably static, mixer.

Advantageously, stage (d) of drying by atomization uses a spray device, also called atomizer, in particular of the turbine or monofluid nozzle type, projecting the product resulting from stage (c) in the form of droplets into a drying chamber. As seen above, preferably, the mixture to be sprayed exhibits a viscosity of at most 300 cP at the inlet of the device in question. The atomization temperature can be between 200 and 350° C. and the mean residence time in the atomizer is generally short, of at most 30 seconds.

Another subject matter of the invention is the support for a catalyst of a reaction of Fischer-Tropsch type obtained by the process described above, and which is provided in the form of a powder with a particle size distribution of between 30 and 120 µm, in particular centered on 80 µm (this sizing being comparable to a diameter of particles which, in this instance, are close to the shape of spheres).

Another subject matter of the invention is the support for a catalyst of a reaction of Fischer-Tropsch type obtained by the process described above, and which is provided in the form of a silica-alumina powder, with a silica content by weight of between 6% and 12%, in particular between 8% and 10%.

Another subject matter of the invention is a process for the preparation of a catalyst of Fischer-Tropsch catalyst type, where the catalyst support obtained according to the process described above is treated with active agents of the type of metals or their precursors.

Another subject matter of the invention is a plant for the preparation of a support for a catalyst of a reaction of Fischer-Tropsch type, said support comprising alumina and silica or their derivatives, starting from:
  a first reactant comprising an alumina compound or precursor in suspension, in particular an aluminum oxyhydroxide, and optionally alumina,
  and a second reactant based on silicic acid and/or on a compound or precursor of silicic acid, and optionally silica, in suspension or dissolved in a solvent. The plant according to the invention comprises:
  a first reactor in which a stage (a) of preparation of the first reactant is carried out, including a reaction for peptization of an alumina compound or precursor,
  a second reactor in which a stage (b) of treatment of the second reactant is carried out, including a controlled aging treatment of the silicic acid aimed at its polymerization up to a degree of conversion of the silicic acid of at most 70%,
  a mixer or group of mixers carrying out a stage (c) of mixing, in particular continuously, the two reactants resulting from the two reactors and in which the reaction between the two reactants takes place, the first reactor and the second reactor each being in fluidic connection with the mixer/group of mixers, with means for regulating the pH of the first reactant in the first reactor or in the mixer or in the fluidic connection means between the first reactor and the mixer,
  a unit for drying, by atomization, the product in the form of particles in suspension in a liquid phase resulting from the mixing stage (c) in order to obtain a powder.

The plant can additionally comprise means for regulating the flow rates of the first and second reactants at the inlet of said mixer/group of mixers, the first reactor and the second reactor each being in fluidic connection with the mixer/group of mixers.

Another subject matter of the invention is the use of the process or of the plant described above for producing a catalyst of the Fischer-Tropsch catalyst type.

DESCRIPTION OF THE EMBODIMENTS

The invention will be described in detail below with the help of nonlimiting examples illustrated by the following figures:

LIST OF THE FIGURES

Figure 1:
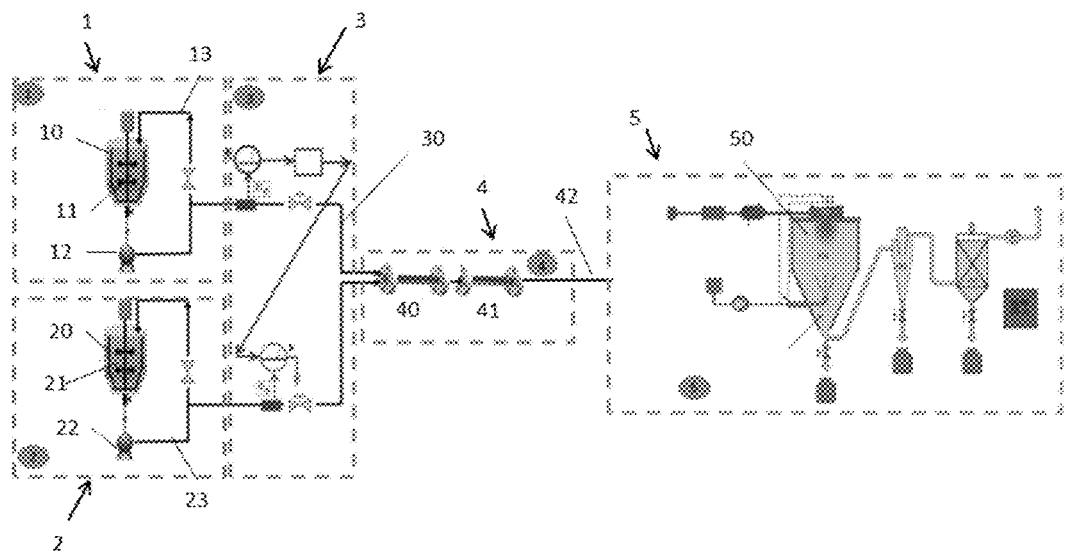
FIG. 1 represents a diagrammatic representation of the complete process for the synthesis of particles of catalyst support in the form of a block diagram according to the invention.

FIG. 1 very diagrammatically represents the different stages of a process for the synthesis according to the invention of a Fischer-Tropsch catalyst support based on alumina and silica starting from boehmite and silicic acid, by dividing it into 5 blocks numbered 1 to 5 in FIG. 1, from the most upstream stage to the most downstream stage of the process:

- Block 1: stage (a), with a stirred vessel for the preparation of alumina from a first reactant, boehmite
- Block 2: stage (b), with a vessel for the preparation of the second reactant, silicic acid
- Block 3: intermediate stage of regulation of injection of boehmite and silicic acid in order to respect a target ratio
- Block 4: stage (c) of injection of the streams originating from blocks 1 and 2 into a group comprising a disperser mounted in series with a static mixer
- Block 5: stage (d) of drying by atomization the suspension resulting from block 4.

It should be noted that the term "vessel", in this instance, denotes a reactor in general, which can be a simple batch treatment vessel or a continuous treatment reactor, in particular.

Details are now given of these blocks successively:

Block 1: stage (a) of peptization of boehmite by addition of nitric acid. The peptization is carried out in a vessel 10 provided with mechanical stirring means 11 which ensure the suspension of the boehmite in powder form in water and sufficient shearing to keep the boehmite in suspension and to peptize it.

An example of a vessel is as follows:
- the vessel 10 has a capacity of 30 liters, the liquid height in the vessel is equal to the diameter of the vessel
- the vessel 10 can, if appropriate, be thermostatically controlled. The peptization reaction can be carried out at ambient temperature and does not need to be thermostatically controlled.

However, it might be necessary to control the temperature and to thermostatically control the jacketed vessel.
- the stirring means 11 are stirring impellers sold by Lightnin or turbines with inclined blades: preferably, the height of the impeller with respect to the bottom of the vessel is in a 1/3 ratio. The motor driving these stirring means 11 can ensure a wide range of stirring speeds, for example between 50 and 500 rpm.
- baffles can be provided in the vessel, for example in the form of baffles detached from the wall and held by the lid of the vessel (not represented)
- a pump 12 is also provided, which is used both to feed the static mixer of block 4 (flow rate, for example, 5-20 l/h) but also to ensure optional recycling around the vessel, via the recycling line 13, which can constitute a means of regulating the exiting flow rate of the vessel (maximum flow rate 50 l/h). High-pressure pumps, of screw pump type or other, are preferable because they make it possible to control the flow rate, to overcome the pressure drop of the downstream line (flow meter, mixer and disperser, atomization device). The objective is to have a pressure of approximately 10 bar (5 to 15 bar) in front of the atomization device of block 5.
- the optional recycling line 13 has a return to the top of the vessel 10 dipping into the liquid (in order to avoid injecting bubbles).
- a valve is also provided, for example on a roundabout (at blocks 1 and 2 in the figure). This control valve makes it possible to adjust the pressure upstream of the atomization device of block 5.
- a discharge valve can be provided (at block 3 in the figure) in order to reduce the time required to stabilize the system.

Operating mode: The action of the nitric acid on the boehmite modifies its surface state and makes possible its at least partial peptization. In this instance, the reactant is boehmite, an alumina precursor. It is also possible to add alumina, which is thus already transformed, to the boehmite at this stage. The peptization takes place in the following way: a water+$HNO_3$ mixture is prepared in the vessel 10, then the boehmite is gradually added and the mixture is kept stirred in the vessel for approximately 30 minutes.

Block 2: Stage (b) with Vessel (20) for Storage of the Silicic Acid
- the silicic acid is prepared upstream from sodium silicate, then passed through an ion exchange resin in order to remove the sodium ions.

This two-stage preparation is carried out in the following way: Sodium (meta)silicate is a strong base forming highly alkaline solutions (pH 13 in 1% solution). It is formed naturally by reaction of silica (silicon dioxide) with sodium carbonate in the molten state. Sodium silicate and carbon dioxide are obtained according to the following reaction:

$$Na_2CO_3 + SiO_2 \rightarrow Na_2SiO_3 + CO_2$$

It is found in two main forms: an anhydrous form (it then exists as a translucent to white crystalline solid of formula $Na_2SiO_3$) and a hydrated form ($Na_2SiO_3 \cdot nH_2O$); it is then sometimes described as "liquid glass" or "water glass".

The silicate is subsequently neutralized by an acid and leads to the formation of silanol groups by hydrolysis (silicic acid): the acidification is carried out by passing through an ion exchange resin which makes it possible to remove the sodium ions and replace them with $H^+$ ions.

Consequently, the silicic acid monomers group together to form Si—O—Si bonds and constitute the silicic acid which is used in stage (b).

During stage (b) and in accordance with the invention, the controlled aging of the silicic acid obtained will be carried out as indicated above: this is a thermal aging, which can be carried out directly in the vessel 20, a closed reactor, of block 2 or which can be carried out in a different reactor which subsequently feeds the vessel 20, for example. It is also possible to envisage that the vessel 20 is a reactor operating continuously in which the aging of the silicic acid takes place, with feeding at the outlet to the means of mixing with the other reactant.

In the nonlimiting case described below, the controlled aging and the optional storage before mixing with the other reactant take place in a single closed reactor, which is the vessel 20, in block 2.

The targeted degree of conversion must be less than 70% and in particular less than or equal to 50%, in order to prevent the rise in gel, and preferably between 10% and 40%.

This conversion is monitored by the measurement of viscosity, determined as follows:

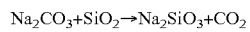

$$\ln(n_r) = (2.50)/(1 - K_1 C) \tag{B}$$

with C the gel fraction value. C can be estimated by virtue of Mooney's equation, it being assumed that the gel domains are spherical and of uniform size, C being determined by virtue of the relationship (B) above, with $K_1$ a constant equal to 1.43 and with $n_r$ the ratio of the dynamic viscosity (µ, in cP) of the sol during gelation to the initial viscosity of the sol ($\mu_0$, in cP), as indicated in the relationship (C) below:

$$n_r = \mu/\mu_0 \tag{C}$$

The aging times are determined in order to achieve the target conversions at a given temperature. Thus, the silicic acid can be aged for a time 4 to 6 times shorter at 60° C. than at 10° C. for one and the same degree of conversion.

This aging operation can be carried out in closed mode or in continuous mode, in a way known to a person skilled in the art.

In closed mode, this operation can, for example, be carried out directly in the reactor/vessel 20 of block 2. Block 2 is, for example, regulated at 10° C. because, at this temperature, the conversion of the silicic acid is slow. The aging is then carried out by a temperature window making it possible to bring the silicic acid to the desired temperature (greater than 10° C.) for a given time and then to bring the temperature of block 2 back to the regulation temperature of 10° C.

In continuous mode, the silicic acid can, for example, pass through a plug-flow reactor thermostatically controlled at the desired temperature with a residence time equal to the desired aging time.

- The concentration of the silicic acid in the vessel 20 before mixing with the other reactant is of the order of 50 g/l and the pH is set in the vicinity of 3.
- the vessel 20 has, for example, a capacity of 10 l, with a height of liquid equal to the diameter of the vessel.
- the vessel 20 is thermostatically controlled with a cold unit making it possible to maintain a temperature between 5° C. and 10° C., in particular 10° C., except during the controlled aging. This is because, the silicic acid having undergone controlled aging beforehand, it is thus useful to have a cooled vessel in order to stabilize the aging of the silicic acid solution at the desired degree of conversion.
- the vessel 20 is stirred, in order to have good temperature homogeneity, by being provided with stirring means, for example in the form of a marine propeller or of the type sold by Lightnin:

preferably, the height of the impeller with respect to the bottom of the vessel is in a 1/3 ratio. The motor driving the impeller is capable of ensuring a wide range of stirring speeds between 50 and 500 rpm.

- baffles can be provided in the vessel 20, for example baffles detached from the wall and fixed to the lid of the vessel.
- a pump 22 is provided: it is used both to feed the static mixer of block 4 (flow rate of between 0.5 and 5 l/h) but also to ensure optional recycling around the vessel 20 (which is a means for flow regulation of the coinjection of the two effluents from the vessels 10 and 20 of blocks 1 and 2 to the mixer of block 3, with a maximum flow rate of 50 l/h). High-pressure pumps, of screw pump type, are preferable because they make it possible to control the flow rate, to overcome the pressure drop of the downstream line (flow meter, mixer and disperser, atomization device).
- the objective is to have a pressure of approximately 10 bar (5 to 15 bar) at the inlet of the atomization device of block 5.
- a valve is provided on a roundabout. This control valve is used to adjust the pressure upstream of the atomization device of block 5. An optional discharge valve is desirable in order to reduce the time required to stabilize the system.
- An insulated recycling line is optionally provided (line diameter approximately 1 cm, for example) with a return to the top of the reactor 20 dipping into the liquid (in order to avoid injecting bubbles).

This stage (b) is thus a stage of aging the silicic acid, followed by an optional cold storage (maintaining the solution at approximately 10° C. in this instance) of the latter.

Block 3: Regulation of the Injection Flow Rates of Boehmite and Silicic Acid

This type of regulation is based on servo-controlled valves and requires two flow meters and a valve on the servo-controlled line (in this instance, that of the silicic acid). A manual control valve is, for example, arranged in parallel with the regulating valve so as to widen the operating valve coefficient.

The regulation of the flow rates is important because it makes it possible to maintain a ratio between the two reactants (suspension of boehmite and silicic acid), despite the possible change in the viscosity of the silicic acid.

The flow rate of boehmite is fixed and that of silicic acid is servo-controlled in order to maintain a ratio R, for example between 2.8 and 3.5, in particular in the vicinity of or equal to 3.

Block 4: Injection of the Two Flows of the Lines 30 and 31 Originating from Block 3 into a Static Mixer At the inlet of the mixer, each flow of the lines 30 and 31 can be interrupted by quarter-turn valves (in order to avoid a return from one line to the other during the start-up and shut-down phases).

The configuration envisaged involves two consecutive static mixers 40, 41 serving respectively:

- as zone for dispersion of the silicic acid in the boehmite suspension for the reaction
- as zone for mixing the polysilicic acid/boehmite product A pressure measurement is provided upstream and downstream of the static mixers 40, 41.

The static mixers of block 4 are positioned as close as possible to the atomization device of block 5, so as to reduce to a minimum the residence time after the mixing zone preceding the drying. If the reaction requires a longer residence time, the static mixers are placed further from the atomization device, so as to leave an additional length, for example of 1 to 3 m, of pipe before atomization.

Block 5: Spray Drying of the Suspension

Once the suspension has been prepared, it is conveyed by a common line 42 via the static mixers 40, 41 to the chamber 50 of the atomization dryer so as to be sprayed as fine droplets which, after evaporation of the solvent, form solid particles. The spraying process is targeted at obtaining liquid droplets or filaments by passing through a local deformation which leads to the atomization. The main parameters which influence the spraying are: the properties of the fluid (density, viscosity, surface tension); the properties of the nozzle (spray angle, spray shape, size of the orifice); the operating parameters (pressure and flow rate of the fluid, temperature). The drying chamber 50 exhibits all the items of equipment known to a person skilled in the art necessary for the generation of the spray fed with hot air; it is followed by a line of cyclones in order to carry out the gas/solid separation.

Two devices for spraying the suspension were used:

- Turbine (preferred mode). The peripheral speed at the atomization wheel conventionally varies between 10 and 200 m/s. Such spray systems make it possible to obtain a homogeneous jet. In this case, the distribution in drop sizes depends predominantly on the rotational speed of the turbine and very little on the pressure. It is thus pointless to add a pump upstream of the atomizer.

With this type of spraying, which radially ejects the particles, it will be necessary to control the severity of the drying in order to ensure that the particles have formed a crust before touching the wall and thus to avoid fouling.

Monofluid nozzle: the flow rate is adjusted by a screw pump in order to maintain an appropriate pressure. It is possible to adopt a cocurrent configuration or, preferentially, to pass in countercurrent, also called fountain mode, in order to increase the residence time.

For this atomization, the aim is to dry the suspension below the bubble point (to avoid internal boiling in the drop). The atomization is preferably carried out between 200 and 400° C. The residence times can vary from a few seconds to one minute (for example, conventionally 25 seconds). The atomization is carried out if the viscosity of the suspension is below 800-1000 cP at the atomization nozzle, ideally below 300 cP, which is the case of the suspension prepared according to the invention and originating from the preceding blocks.

EXAMPLES

The examples make use of the results of a rheokinetic study (shear 30 s$^{-1}$) which made it possible to measure the viscosity of the reactive mixture between the peptized boehmite and the silicic acid over time. The ratio of the flow rates by volume is 3.22 (Q boehmite/Q silicic acid). The cell is a controlled strain rheometer (TA Instruments ARES) equipped with a single helical ribbon and with a 30 ml flat-bottomed vessel which is thermostatically controlled by the Peltier effect at 10° C.

Tests were carried out to define the viscosity windows where the mixture is atomizable. In the following examples, the preparation of the reactants, peptization of the boehmite, on the one hand, and preparation of the silicic acid from silicate on ion exchange resins, on the other hand, strictly follows the same protocol (see below).

Peptization of the boehmite (block 1):
Nature of the boehmite: boehmite sold by Axens under the trade name GA7001 (any other boehmite also being able to be suitable)
Amount of boehmite: 13% by weight (the rest is made up of water). Preferably, for the boehmite GA7001, it remains less than 22%.
Nitric acid: 9% equivalent weight/boehmite (other acids may also be suitable, such as weak or strong acids, inorganic or organic acids).

The mixture is stirred at 10° C. for 45 minutes. At the end of the peptization, the pH of the solution is equal to 3. By adsorption of H+ ions on the crystal faces, without any particular action, the pH tends to rise over time: after 5 hours, the pH has gone from 3 to 3.5, then it tends toward 3.8 after 10 hours.

According to the examples in accordance with the invention indicated below, at the end of the peptization, the pH of the solution is maintained in the vicinity of 3 during its preparation until the mixing with the silicic acid. Alternatively, it is brought back to the vicinity of 3 before mixing with the silicic acid if it has not been maintained at this pH during the peptization (if the pH during the peptization is markedly greater than 3 while remaining acidic): in both scenarios, it is maintained at/reduced to 2.86, a value close to the isoelectric point of silicic acid, in the following two examples. (The same results are obtained by maintaining the pH at/bringing the pH back to the value of 3, which is the isoelectric point, or values a little higher than this isoelectric point and of at most 3.1 or 3.2).

Example 1 (Comparative)

In example 1, the silicic acid is mixed with the other reactant once peptized without prior aging according to the invention. This is then referred to as "fresh" silicic acid, that is to say without intermediate storage or at most intermediate storage of a few hours at a temperature of at most 10° C. (between 0 and 10° C.). The silicic acid solution is at 60 g/l and its degree of conversion/condensation is thus equal to or in the vicinity of 0%.

Example 2 (The Invention)

In this example 2, the silicic acid is aged beforehand at 10° C. for 24 hours, with a conversion of the silicic acid of 15%.

Figure 2:
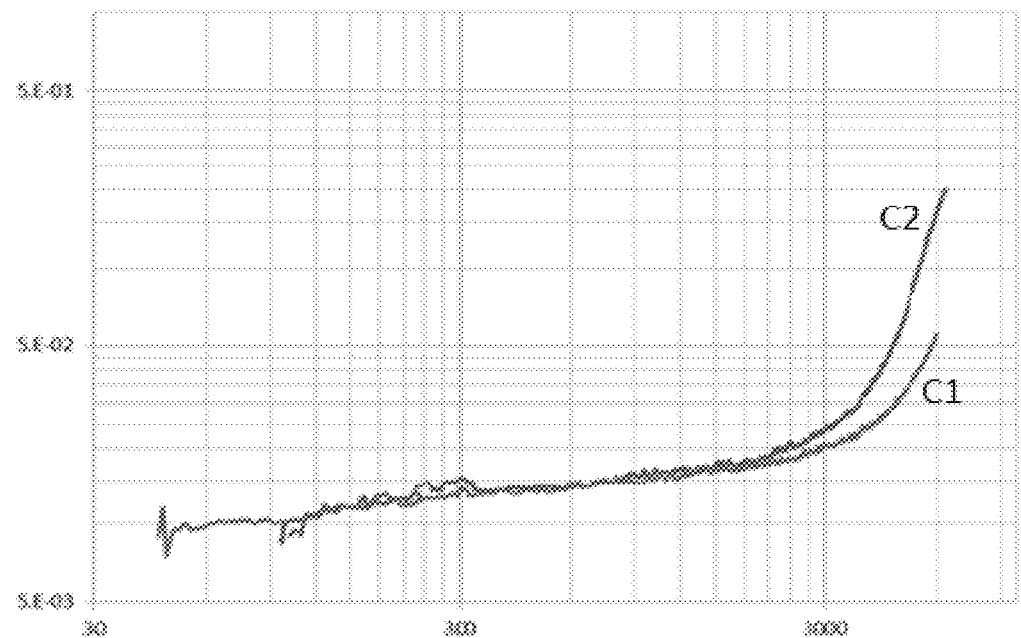
FIG. 2 represents a graph representing, for examples 1 and 2, the change in the viscosity, expressed in Pa·s, as a function of time, expressed in seconds, of the mixture obtained at the end of stage (c).

FIG. 2 illustrates the rise in viscosity over time of the mixtures according to example 1 (curve C1) and according to example 2 (curve C2): In the case of example 1, the mixture leads to a low viscosity, below 30 cP. The viscosity does not exceed 50 cP after 3000 s. In the case of example 2, the mixture leads to a slower rise in the viscosity, which does not exceed 50 cP for the duration of the experiment. It is thus demonstrated that the same viscosity is obtained whether "fresh" silicic acid or silicic acid aged according to the invention is used, with the advantage, for the aged silicic acid, of a lower viscosity after 3000 seconds, optionally making it possible to further defer, if need be, the subsequent atomization stage. The powder grains obtained for examples 1 and 2 are regular and approach a spherical shape, their silica content is 9.75% by weight and their alumina content is 90.25% by weight. It is by virtue of the invention that it is possible to carry out a drying by atomization which makes it possible to obtain, in comparison with other drying processes, particles of more spherical and more regular shape and of more reproducible mean size.

Example 3 (According to the Invention)

This example 3 reproduces example 2, while modifying the conditions of the aging: in this instance, the silicic acid is aged beforehand at 60° C. for 4 hours, with a conversion of the silicic acid of 15%.

The results obtained are comparable to those obtained with example 2.

Example 4 (According to the Invention)

This example 4 reproduces example 3, while modifying the conditions of the aging: in this instance, the silicic acid is aged beforehand at 80° C. for 3 hours, with a conversion of the silicic acid of 15%.

The results obtained are comparable to those obtained with example 3.

In examples 5 and 6 below, unlike examples 1 to 4, at the end of the peptization, the pH of the boehmite solution is equal to 3.86 and is not maintained at 2.86. They show the impact of the aging of the silicic acid mixed with a first reactant peptized at higher pH, at a pH markedly greater than the isoelectric point (equal to 3) of silicic acid.

Example 5 (Comparative)

The conditions are the same as for example 1, with the use of a "fresh" silicic acid (0% conversion), except that the first reactant is at pH 3.86 during the mixing of the two reactants.

Example 6 (Comparative)

The conditions are the same as in the case of example 3, with silicic acid aged at 60° C. for 4 hours, to reach 15% conversion of the silicic acid, except that the first reactant is at pH 3.86 during the mixing of the two reactants.

Figure 3:
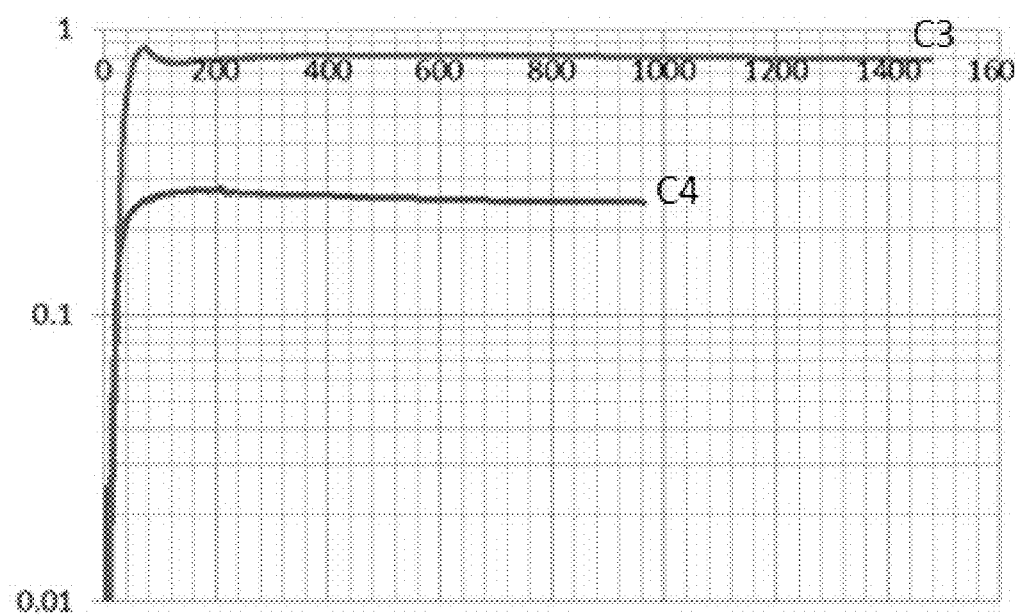
FIG. 3 represents a graph representing, for examples 3 and 4, the change in the viscosity, expressed in Pa·s, as a function of time, expressed in seconds, of the mixture obtained at the end of stage (c).

As illustrated in FIG. 3, for these examples 5 (curve C3) and 6 (curve C4), the mixture rises rapidly in viscosity and reaches in a few seconds the range of "non-atomizability" (it is impossible to atomize the mixture at such viscosity levels) because the pH of the mixture in both cases is too high, above the isoelectric point of silicic acid. The plateau reached is, however, lower in the case of the converted silicic acid of example 4.

In conclusion, the aging (the partial conversion) of the silicic acid makes it possible both to extend the time for rise in viscosity of the reactive mixture of boehmite and silicic acid and to lower the viscosity of the final viscosity plateau of this, which is what makes it possible to be able to use the technology of atomization to make the grains from this mixture. In addition, it has been shown that, to do this, it is also important to control the pH of the mixture and that the most effective way of doing it is to control/regulate the pH of the alumina-based reactant, in particular in the vicinity of the isoelectric point of silicic acid (pH=3).

The invention thus makes it possible to control the viscosity of each of the reactants, one by controlled aging and the other by adjusting its pH, in order for the mixture to react without exceeding the maximum viscosity desired for the continuation of the process. The viscosity of the mixture is thus lowered, in comparison with a process without aging, and it also tends to "rise" later in time.

The invention claimed is:

1. A process for preparing a catalyst support for a reaction of Fischer-Tropsch type in the form of a powder, said support comprising alumina and silica and/or one or more derivatives thereof,
wherein the process comprises:
  a stage (a) of preparing a first reactant, which first reactant comprises an alumina compound or precursor, and optionally alumina, in suspension in a solvent, wherein said preparing of the first reactant occurs in a first reactor (10), including a reaction for peptization of the alumina compound or precursor, in the presence of an acid, so as to form solid particles in at least partially colloidal suspension,
  a stage (b) of preparing a second reactant, which second reactant is based on silicic acid and/or on a compound or precursor of silicic acid, and optionally silica, in suspension or dissolved in a solvent, wherein said preparing of the second reactant occurs in a second reactor (20), including a controlled aging treatment of the silicic acid targeted at its polymerization up to a degree of conversion of the silicic acid of at most 70%, said second reactant resulting from stage (b), which is at a pH of at most 3.4,
  a stage (c) of mixing the two reactants resulting from the two reactors in a mixer or group of mixers (40, 41), in which the reaction between the two reactants takes place,
and wherein the pH of the first reactant is adjusted to a value not exceeding a given maximum pH threshold ($pH_{max}$), said threshold having a value equal to 3.4, before its introduction into the mixer in the mixing stage (c), in order to obtain a mixture in the form of particles in suspension in a liquid phase.

2. The process as claimed in claim 1, wherein the controlled aging treatment is carried out at a temperature of between 5° C. and 90° C.

3. The process as claimed in claim 1, wherein the controlled aging treatment is carried out up to a degree of conversion of the silicic acid of at least 10%.

4. The process as claimed in claim 1, wherein the controlled aging treatment is carried out at a concentration of silicic acid in the liquid phase of the second reactant of between 30 g/l and 200 g/l.

5. The process as claimed in claim 1, wherein the controlled aging treatment is carried out batchwise, in a closed reactor, or continuously.

6. The process as claimed in claim 1, wherein the pH of the first reactant is adjusted to a value equal to +/−15% of the isoelectric point of silicic acid.

7. The process as claimed in claim 1, wherein the pH of the first reactant is adjusted during all or part of stage (a) of its preparation and/or at the end of stage (a) and/or after stage (a) and before stage (c).

8. The process as claimed in claim 1, wherein the peptization reaction uses boehmite, in the presence of an acid.

9. The process as claimed in claim 1, wherein the second reactant, resulting from stage (b), is at a pH of at most 3.2.

10. The process as claimed in claim 1, wherein the mixing stage (c) takes place continuously in the mixer or the group of mixers (40, 41) in which the reaction between the two reactants takes place.

11. The process as claimed in claim 1, wherein the mixing stage (c) takes place with regulation of the input flow rates of the first and second reactants at the inlet of said mixer/group of mixers.

12. The process as claimed in claim 1, wherein the viscosity of the mixture produced in stage (c) is less than or equal to 300 cP.

13. The process as claimed in claim 1, wherein the viscosity of the second reactant on conclusion of stage (b) remains, before mixing of stage (c), at a viscosity of less than or equal to 250 cP.

14. The process as claimed in claim 1, further comprising:
  a stage (d), which takes place continuously following the mixing stage (c), wherein stage (d) is a stage of drying by atomizing the mixture resulting from the mixing stage (c) in order to obtain a powder.

15. The process as claimed in claim 1, wherein the alumina compound or precursor is aluminum oxyhydroxide.

16. The process as claimed in claim 1, wherein the mixing stage (c) takes place with regulation of the input flow rates of the first and second reactants at the inlet of said mixer/group of mixers, which is carried out by subjecting one of the flow rates of reactants to the control of the other.

17. The process as claimed in claim 1, wherein the controlled aging treatment is carried out continuously with a thermostatically controlled plug-flow reactor.

18. The process as claimed in claim 1, wherein the controlled aging treatment is carried out at a temperature of between 45° C. and 65° C.

19. The process as claimed in claim 1, wherein the peptization reaction uses boehmite in the presence of an nitric acid.

20. The process as claimed in claim 1, wherein the controlled aging treatment is carried out up to a degree of conversion of the silicic acid of between 10% and 40%.

* * * * *